United States Patent
Kabir et al.

(10) Patent No.: US 9,851,281 B2
(45) Date of Patent: Dec. 26, 2017

(54) IN-VIAL MICROEXTRACTION (IVME) SYSTEMS AND THEIR METHOD OF MAKING

(71) Applicants: Abuzar Kabir, Dhaka (BD); Kenneth G. Furton, Homestead, FL (US)

(72) Inventors: Abuzar Kabir, Dhaka (BD); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/242,809

(22) Filed: Aug. 22, 2016

(65) Prior Publication Data

US 2017/0003205 A1    Jan. 5, 2017

(51) Int. Cl.
| | | |
|---|---|---|
| B01L 3/08 | (2006.01) | |
| B01L 3/14 | (2006.01) | |
| G01N 1/40 | (2006.01) | |
| B01L 3/00 | (2006.01) | |
| G01N 30/00 | (2006.01) | |
| G01N 30/06 | (2006.01) | |

(52) U.S. Cl.
CPC ........... G01N 1/405 (2013.01); B01L 3/5082 (2013.01); *B01L 2200/0631* (2013.01); *B01L 2300/069* (2013.01); *B01L 2300/0858* (2013.01); *G01N 2030/009* (2013.01); *G01N 2030/062* (2013.01)

(58) Field of Classification Search
CPC ............ G01N 1/405; G01N 2030/009; G01N 1/0095; B01L 3/08; B01L 3/14
See application file for complete search history.

(56) References Cited

U.S. PATENT DOCUMENTS

| | | | | |
|---|---|---|---|---|
| 2002/0150923 A1* | 10/2002 | Malik | ................... | B01J 20/103 435/6.1 |
| 2005/0059162 A1* | 3/2005 | Wohleb | ............... | B01L 3/50825 436/177 |
| 2005/0276727 A1* | 12/2005 | Pawliszyn | .......... | A61B 5/14514 422/537 |
| 2013/0157254 A1* | 6/2013 | Sengupta | ............. | G01N 21/658 435/5 |
| 2014/0274660 A1* | 9/2014 | Kabir | .................... | G01N 1/405 502/5 |
| 2015/0322489 A1* | 11/2015 | Mische | .................... | C07H 1/06 436/501 |

* cited by examiner

*Primary Examiner* — Jan Ludlow
(74) *Attorney, Agent, or Firm* — Saliwanchik, Lloyd & Eisenschenk

(57) ABSTRACT

An in-vial microextraction (IVME) device is a vial with at least a portion of the inner surface having a sol-gel coating that absorbs at least one target analyte. The sol-gel coating is a metal oxide comprising coating that is formed from a tri- and/or tetra-functional metal comprising precursor that condenses to form a gel network. The IVME device can be used to prepare a sample by the contacting of the IVME device with a solution or suspension. An analytical method is enabled where the absorbed analyte from the IVME device is subsequently desorbed with a solvent or solution or thermally desorbed and analyzed using GC-MS or LC-MS or other analytical instrument for separation and detection.

26 Claims, 3 Drawing Sheets

IN-VIAL MICROEXTRACTION (IVME) SYSTEMS AND THEIR METHOD OF MAKING

BACKGROUND OF INVENTION

Sample preparation is an integral and perhaps the most important step in chemical analysis. A wide variety of samples of environmental, pharmaceutical, toxicological, biological, food, and clinical significance require simple, robust, and inexpensive alternative to current classical sample preparation technologies that are characterized with multi-step, laborious, expensive, and often unreliable results. One approach to sampling is directed to the use of surface-bonded hybrid organic-inorganic polymer coatings and monolithic beds for analytical microextraction. These systems display high chemical stability and offer a diverse array of extracting phases for solvent-free or solvent minimized analytical sample preparation. The availability of a wide variety of sol-gel precursors and sol-gel active organic macromers, oligomers, or dendrimers allow facile synthesis of advanced material systems with unique selectivity, enhanced extraction sensitivity and high thermal, mechanical and solvent stability. These sol-gel derived hybrid organic-inorganic advanced material systems have been shown to be effective in solvent free/solvent minimized sample preparation for a wide variety of analytes with biological, environmental, clinical, toxicological, food, pharmaceutical, bio-analytical, and forensic significance.

Sol-gel technology for the preparation of solid phase microextraction (SPME) sorbents has solved many limitations of conventional coatings. Sol-gel coatings chemically bond to different substrates, such as silica. Gel is formed from the sol solution in the presence of the substrate. Because of the wide variety of possible sol components, sol-gel technology allows the synthesis of a large number of sorbents for SPME and similar microextraction techniques (e.g., capillary microextraction, stir bar sorptive extraction) with large surface area, unique selectivity, and high thermal and solvent stability. Sol-gel monolithic beds are capable of achieving very high sample pre-concentration factors. The versatility of sol-gel technology allows the creation of surface-bonded sorbent coatings on unbreakable fiber materials (e.g., Ni—Ti, stainless steel, titanium, and copper) and also on substrates of different geometrical formats such as planar SPME (PSPME), and membrane SPME (MSPME). Sol-gel technology is adaptable to forming multi-component materials that have customized surface morphologies, selectivities, and affinities of the sorbent. A wide variety of sol-gel silica, titania, zirconia, alumina, and germania-based precursors are commercially available. Additionally, a wide range of sol-gel reactive organic ligands are available to design hybrid organic-inorganic sol-gel coatings that can be used to target a particular analyte or sample matrix with improved selectivity, sensitivity, extraction phase stability and performance.

There remains a strong need for solvent free or solvent minimized microextraction devices that permit the acquisition of low concentrations of analytes present in a wide range of aqueous or other liquid environments. Devices that can be used by untrained individuals to provide truly representative sample and allow the work up of these samples in a simple and effective manner are desirable.

BRIEF SUMMARY

An embodiment of the invention is directed to an in-vial microextraction (IVME) device; where a vial has a sol-gel coating over at least a portion of the inner surface that is capable of absorbing at least one target analyte. The vial can be glass, plastic, ceramic, or metal and the sol-gel coating can comprise a metal oxide comprising gel from a precursor of the structure: $R^1R^2R^3R^4M$, wherein: $R^4$ is optional; M is silicon, titanium, aluminum, zirconium, germanium, barium, gallium, indium, thallium, vanadium, cobalt, nickel, chromium, copper, iron, lanthanum, niobium, zinc, or boron; at least two of $R^1$, $R^2$, $R^3$, and $R^4$ are independently alkoxy, hydroxy, halides, hydrogen or dialkylamino, and the remaining $R^1$, $R^2$, $R^3$, and $R^4$ are independently substituted or unsubstituted alkyl, aryl, cyanoalkyl, fluoroalkyl, phenyl, cyanophenyl, biphenyl, cyanobiphenyl, dicyanobiphenyl, cyclodextrin moieties, crown ether moieties, cryptand moieties, calixarene moieties, dendrimer moieties, graphene moieties, carbon nanotubes, or wherein the $R^1$, $R^2$, $R^3$, and $R^4$ is chiral or achiral. In addition to the metal oxide precursor a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tri(dialkyamino)alkylsilane, tri(dialkyamino)arylsilane, di(dialkyamino)dialkylsilane, di(dialkyamino)alkylarylsilane, di(dialkyamino)diarylsilane, or any combination thereof can be included, wherein alkyl groups are $C_1$ to $C_4$ alkyl groups and aryl groups are phenyl groups, alkyl substituted phenyl groups, or polycyclic aromatic groups, wherein the alkyl groups and phenyl groups are unsubstituted or independently substituted with amino, hydroxyl, carboxylic acid, acid anhydride, epoxy, acrylate, methacrylate, vinyl, or reaction residue therefrom. An $R^1$, $R^2$, $R^3$, and $R^4$ group can include a bidentate ligand, polydentate ligand, crown ether, cryptand, aryene, graphene, fullerene, hydroxyfullerene, cyclodextrin, or calixarene. The sol-gel coating can also include an organic portion that is oligomeric or polymeric. The inner surface of the IVME device can have a sol-gel coating over the entire surface or only on the walls with no sol-gel coating on its base. At least a portion of the exterior surface can include a sol-gel coating that has a like or different composition to that of the inner surface.

Another embodiment of the invention is directed to a method of preparing an IVME device as above, where a vial has at least one sol deposited on at least a portion of the inner surface of the vial and the sol is transformed by curing into the sol-gel coating. Optionally, any unreacted portions of the sol or non-bound side products formed during curing can be removed from the sol-gel coating. Deposition can be carried out by dip coating, spray coating, painting, or by filling, partially or completely, the vial with a sol solution. Curing can be an acid or a base catalyzed hydrolysis and condensation of at least two of: metal oxide precursors; siloxy precursors; and organic precursors. An addition or polyaddition reaction can be carried out that is catalyzed by an acid, a base, or a free radical initiator.

Another embodiment of the invention is directed to a method of sampling a target analyte, where an IVME device is contacted with a sample matrix suspected of containing the target analyte. The sample matrix is in a fluid state that is a primary liquid, a primary suspension, or a secondary liquid or secondary suspension prepared by combining a primary solid with a provided liquid. The IVME device can be separated from the sample matrix suspected of containing the target analyte. A deuterated standard of a target analyte can be added to the IVME device to which the sample matrix is contacted. The IVME device can be rinsed with a tertiary liquid, either aqueous, organic, or a combination thereof, after removing the fluid that contained the sample matrix.

Another embodiment of the invention is directed to a method of analyzing for a target analyte, where after sampling the sample matrix as above, the target analyte(s) are desorbed from the IVME device thermally or by contacting one or more solvents and/or solutions, either simultaneously or sequentially, to the IVME device to form one or more analyte solutions that is introduced through an inlet to an analytical instrument. The analytical instrument can be a GC, LC, IMS, capillary electrophoresis unit, mass spectrometry (MS), GC-MS, or LC-MS.

DETAILED DISCLOSURE

Figure 1:
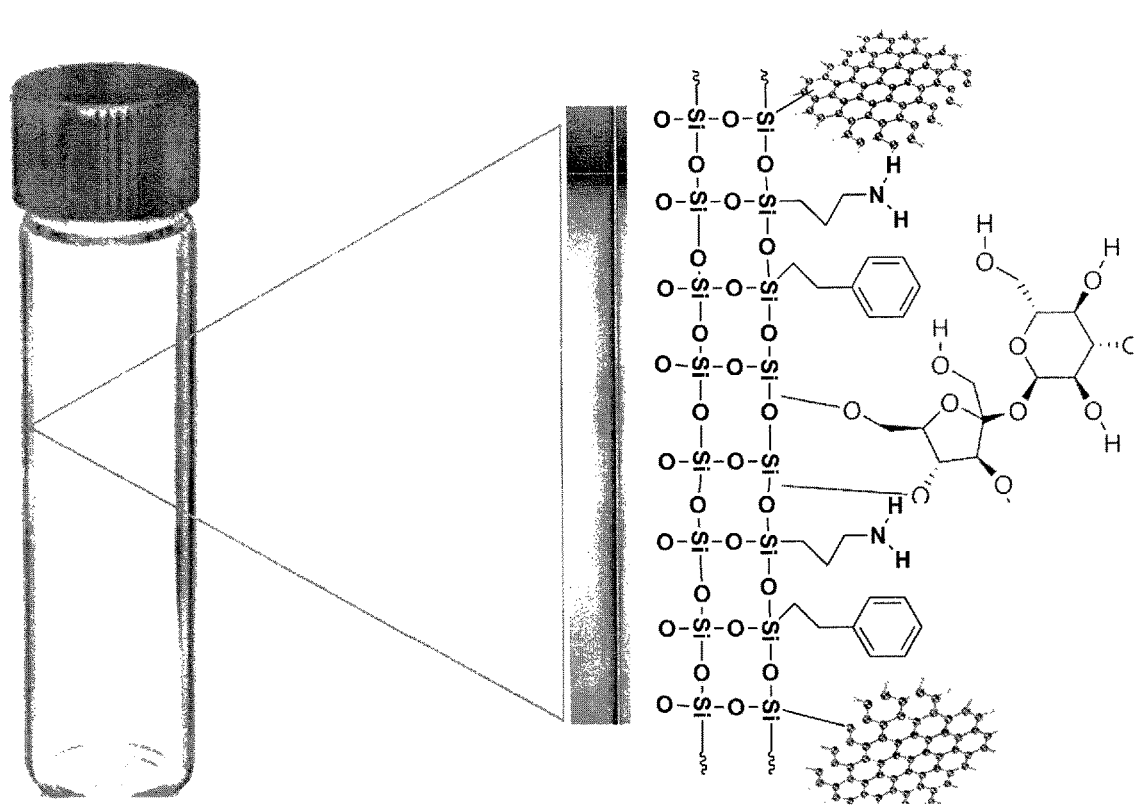
FIG. 1 shows a vial and a highlight of a sol-gel coating on the inner surface with an exemplary chemical structure of the gel that comprises an IVME device, according to an embodiment of the invention.

Embodiments of the invention are directed to an in-vial microextraction (IVME) method that uses IVME devices that are sample collection vials, which can be of different size, shape, and construction materials, having a sorbent coating on at least a portion of the inner surface of the vial. The sorbent coating is constructed on the surface of the vial using sol-gel coating technology, as illustrated in FIG. 1 for a silicon oxide based coating on an inner surface of a vial. In an embodiment of the invention, the vial is a cylindrical container of plastic/metal/glass or other composite materials, which acts as the for the internal sol-gel coating. In other embodiments of the invention, the vial can be square or rectangular in shape. The sample is a fluid sample that can be collected in the IVME device at the field or a fluid that is placed in the IVME device at a site that is other site of the source such as a laboratory, the sorbent coating spontaneously extracts the analyte(s) until equilibrium partitioning of the target analyte between the extraction sorbent and the fluid sample matrix is achieved. The fluid sample can be aa primary liquid solution, for example, but not limited to, an aqueous solution, a primary liquid suspension, for example, but not limited to, an aqueous suspension, that is collected as a fluid from the sample source location or it can be a secondary liquid or secondary suspension, where a solid sample from the sample source location is mixed with a provided liquid that can be water, an aqueous solution, an organic solvent, or an organic solution to result in the secondary solution or suspension, depending on the solubility of components of the primary solid sample in the provided liquid. The rate at which extraction equilibrium is achieved can be enhanced by stirring the fluid using a magnetic stir bar placed on a magnetic stirrer, shaking by hand, or otherwise agitating using, for example, an orbital shaker. Once extraction equilibrium is reached, the fluid sample can be removed, and, if desired, a second fluid sample can be placed in the same IVME vessel and the extraction repeated using the same sorbent; which can allow the sampling of very dilute target analytes with a gel coating that can absorb much more than could be absorbed in a single extraction. Generally, the extraction will achieve equilibrium within a few minutes, and knowledge of the rate of absorption by a targeted analyte and the gel coating can be predetermined and the extraction protocol provide to the sampling technician.

An analyte extracted into the sorbent coating inside the IVME device can be eluted employing a solvent mediated back-extraction or by thermal desorption. In solvent mediated back-extraction, a small volume of organic solvent is placed into the IVME device and contacted, often with a vortex imposed, for a short period of time for desorption of the extracted analytes into the organic solvent. Organic solvents that can be used include, but are not limited to: aliphatic hydrocarbons, aromatic hydrocarbons, ethers, esters, alcohols, ketones, and other solvents that are identified to be preferable for a given target analyte. Mixed solvents can be used, and a plurality of selective solvents can be sequentially used to remove a sequence of analyte solutions of differing composition. Aqueous solutions can be used for analytes that would partition into the aqueous solution having a component that has a specific affinity for the target analyte.

Figure 3A:
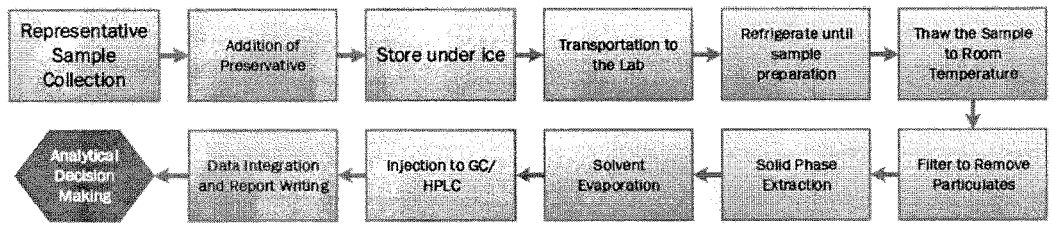
FIG. 3A shows a flow chart of currently practiced analytical procedure from field sampling, to solid-phase extraction, through analysis.
Figure 3B:
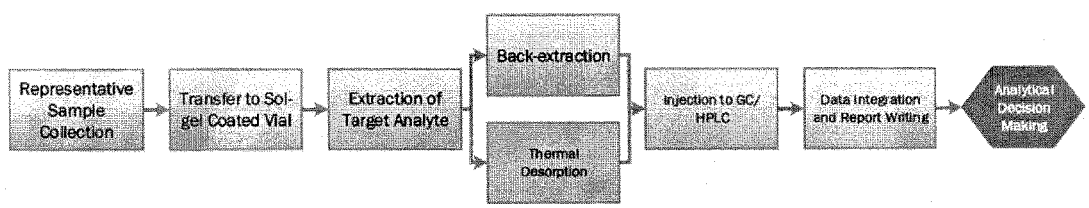
FIG. 3B shows a flow chart of an analytical procedure where field sampling includes or is followed by in-vail microextraction (IVME), and analysis, according to an embodiment of the invention.

A back-extraction solution of a target analytes can be centrifuged to separate any particulate matter from the solution and subsequently the particle free solution can be injected into gas chromatography or liquid chromatography for analyte detection and quantitation. By placing an IVME device in a high temperature source, such as a thermal desorption unit (TDU) employing a continuous flowing carrier gas as a purge, one or more analytes can be introduced into the inlet of a gas chromatography system. Analytes can be focused into a GC inlet by cryofocusing techniques and subsequently introduction onto a GC column by increasing the GC inlet temperature. The IVME system using the IVME device drastically reduces the number of steps, time, cost, and organic solvent consumption required for contemporary sample preparation practice, as indicated in FIG. 3A and FIG. 3B, for current and IVME methods, respectively. By totally eliminating several steps, such as: sample transportation to the analytical lab in different containers; storing the aqueous samples at controlled laboratory environment prior to the sample preparation and analysis; utilizing a number of glassware in the entire sample preparation exercise; and solvent evaporation from the eluent followed by sample reconstitution, a tremendous improvement to the overall quality and integrity of the analytical data collected over conventional sample preparation techniques is possible because many of the aforementioned steps contribute to significant loss of the target analytes.

To form the sol-gel sorbent coating on the IVME device, the sol can comprise precursors to gels of silica, titania, alumina, zirconia, germania, barium oxide, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or any combination thereof. A sol solution used to form the gel on the surfaces of a vial can employ an organic solvent and water, for example an alcohol, such as ethanol, and sufficient water to condense the sol to a gel. In an embodiment of the invention, where a tetravalent metal, such as, but not limited to, silicon and titanium is used, the precursors used to generate the sorbent coating have the general structure: $R^1R^2R^3R^4M$, wherein, M is the precursor-forming element taken from any metal oxide, but not limited to, metal oxides listed above. Substituent groups $R^1$, $R^2$, $R^3$, and $R^4$ include at least two of which are sol-gel active. As can be appreciated by one of ordinary skill in the art, for a trivalent metal, for example, but not limited to aluminum, only $R^1$, $R^2$, and $R^3$ are present, and in this respect, $R^4$ is optional in the formula. Embodiments of the invention are herein described with respect to the metal of the precursor being silicon, but one should appreciate that the structures described for silanes can be employed with other precursors and mixtures of precursors that are of different metals. Sol-gel active groups include, but not limited to, alkoxy, hydroxy, halides, and dialkylamino. Remaining R groups may be non-sol-gel active and may include alkyl moieties and their derivatives, arylene moieties and their derivatives, cyanoalkyl moieties and their derivatives, fluoroalkyl moieties and their derivatives, phenyl moieties and their derivatives, cyanophenyl moieties and their derivatives, biphenyl moieties and their derivatives, cyanobiphenyl moieties and their derivatives, dicyanobiphenyl moieties and their derivatives, cyclodextrin moieties and their derivatives, crown ether moieties and their derivatives, cryptand moieties and their derivatives, calixarene moieties and their derivatives, dendrimer moieties and their derivatives, graphene moieties and their derivatives, carbon nanotubes and their derivatives, chiral moieties and other similar non-sol-gel active moieties.

A silica precursor can be any reactive silane compatible with any solvent of the sol and other components of the sol. For example, the silane can be a tetraalkoxysilane, tetraacetoxysilane, tetrachlorosilane, tetradialkylaminosilane or any other silica precursor. For example, tetramethoxysilane or tetraethoxysilane can be used as a silica precursor. In like manner, a tetraalkoxytitanate can be used as a titania precursor, trialkoxyaluminum can be used as an alumina precursor, and other metal alkoxides can be the source of zirconia, germania, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or barium oxide incorporated into the ultimate gel of the IVME device. Generally, but not necessarily, the alkoxy and dialkylamino groups are $C_1$ to $C_4$ alkoxy and dialkylamino groups.

The sol can further comprise one or more siloxy precursors to the gel where it will be incorporated as monoalkysiloxy, monoarylsiloxy, dialkylsiloxy, diarylsiloxy, or any combination of these precursors within a gel, where the alkyl or aryl groups can be unsubstituted, or substituted with functional groups for modification of the properties of the gel, to promote a specific affinity for one or more analytes, to react with other components included in the sol, and/or to have an affinity for a vial's surface. Hence, the siloxy precursor can be, but is not limited to, a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tridialkyaminoalkylsilane, tri(dialkyamino)arylsilane, di(dialkyamino)dialkylsilane, di(dialkyamino)alkylarylsilane, di(dialkyamino)diarylsilane, or any combination thereof. The alkoxy and dialkylamino groups are generally, but not necessarily, $C_1$ to $C_4$ alkoxy and dialkylamino groups. The alkyl groups are generally, but not necessarily, $C_1$ to $C_4$ groups and aryl groups are generally, but not necessarily phenyl groups. The alkyl and/or phenyl groups can be substituted with a functional group, such as, but not limited to amino, hydroxyl, carboxylic acid, acid anhydride, epoxy, acrylate, methacrylate, and vinyl. The siloxane precursor can be an oligo or polysiloxane that comprises: dialkylsiloxanes; alkylarylsiloxanes; diarylsilanes; alkylhydrogensiloxanes; or any combination thereof. The alky groups include, but are not limited to, methyl, ethyl, n-propyl, isopropyl, n-butyl, sec-butyl, and tert-butyl groups. The aryl groups are generally, but not necessarily, phenyl groups. The oligo and polysiloxanes comprise at least one reactive group, which can be on one or both terminal units, for example an α,ω-dihydroxypolydimethylsiloxane, or can reside on a silicon, alkyl, or aryl group of a repeating unit. Other reactive groups, in addition to hydroxy groups, can reside on terminal or internal silicon atoms of repeating units including, but not limited to, acetoxy, hydrogen, chloro, dialkylamino, and γ-aminopropyl.

The sol can further comprise one or more organic precursors that have functionality that is reactive with the precursor substituents, reactive intermediate substituents, or with the functionality on the siloxy precursors. The organic precursors can be monomeric, oligomeric, or polymeric, where there is at least one functionality on the organic precursor that can react with a reactive precursor substituent, a reactive intermediate substituent, or a reactive functionality of a siloxy precursor in the sol. When the organic precursor has a plurality of functionalities, the organic precursor can react with the functionality of another organic precursor in addition to reacting with a functionality of the sol or the gel that is not of the organic precursor. The organic precursor can have additional functionality for modifying the properties of the gel, functionality that provides an affinity for a target analyte, or functionality that provides an affinity for the surface of the vial. Polymeric organic precursors can be homopolymers or copolymers, and can have a linear, branched, star-branched, hyper-branched, or dendritic structure. The organic precursors, and functional groups on the siloxy precursors, can be reactive functionality that do not involve hydrolysis and can be functionality that undergo addition or polyaddition reactions rather than condensation reactions to be incorporated into the gel. Organic precursors include, but are not limited to, α,ω-dihydroxyalkanes, α,ω-dihydroxy-poly(ethylene oxide), α,ω-dihydroxy-polypropylene oxide, α,ω-dihydroxy-poly(ethylene oxide-co-propylene oxide), α,ω-dihydroxy-poly(butylene oxide), α,ω-dihydroxy-polyamides, and α,ω-dihydroxy-polyesters. Polymers can be of low degree of polymerization and may be oligomers. The organic precursor can include monomers, oligomers, and/or polymers with pendant reactive functionality, for example, but not limited to, a partially hydroxylated polybutadiene. In addition to hydroxy groups, the reactive groups can be complementary reactive functionality to reactive groups of the siloxane precursors, and can be, but are not limited to, amino, hydroxyl, carboxylic acid, acid anhydride, epoxy, acrylate, methacrylate, and vinyl. Monomeric organic precursors include, but are not limited to, divinylbenzene. Oligomeric organic precursors include, but are not limited to, α,ω-diacrylates of oligoesters. Polymeric organic precursors can be homopolymers, random copolymers, alternating copolymers, block copolymers, or graft-copoolymers, and can be linear, branched, hyper-branched, star, or dendritic.

Functionality that provide specific affinity for analytes can include those which provide specific interactions, such as ionic functionalities, ion complexing functionalities, hydrogen bonding, plurally hydrogen bonding functionality, π-stacking functionality, or any other functionality that augments the van der Waals, dipole, induced dipole or other inherent intermolecular forces displayed between the gel and analyte. Functionality that provide specific affinity for analytes include, but are not limited to, bidentate ligands, polydentate ligands, crown ethers, cryptands, aryenes, graphene, fullerenes, hydroxyfullerenes, cyclodextrin, calixarene, and carbon nanotubes. Functionality that provides specific affinity for an analyte can be enantiomeric and not a racemic mixture for chiral selectivity of an analyte.

The sol-gel process is carried out in the vial and can be carried out in a single physical step, for example, contacting the inner surface of the vial with a sol solution comprising all pre-gel precursors. The sol-gel process can be carried out in a plurality of physical steps where a portion of the pre-gel precursors are in an initial vial contacting solution, and after a desired degree of reaction has occurred in that step, additional gel precursors as neat liquids or as solution are added to the vial contacting solution. In this manner, the gelation can occur by a sequence of reactions that would not occur in a single mixture of all sol precursors. As necessary, the first step of the sol-gel process can be a modification of the vial's surface by chemically reacting with the surface, or by depositing a gel precursor that has a strong physical affinity for the vial's surface and is not readily disrupted by subsequent gelation steps or upon use of the ultimate IVME device. The vial containing the sol can be rotated or otherwise agitated during curing.

In addition to the sol-gel precursors, the sol can include one or more agents that promote, initiate, or catalyze reactions to form the gel. For example, acids, bases, or radical initiators can be included. The sol can include agents that are porogens for producing pores, foaming agents, and templates for forming binding sites that bind specific analytes that are absorbed in a specifically shaped and functionalized cavity. For example, the template can form a binding site similar to that found in enzymes and with other biopolymers, such as other proteins and nucleotides. The template can be the analyte or a mimic of the analyte. Indicators can be included in the sols and ultimately in the gel, such that the environment in which the IVME device is employed for extraction of an analyte is reflected. For example, colorimetric indicators can change in color based on the pH or oxidative environment of the target environment, such that these factors and their environment's consequences on the efficiency of the IVME device to absorb the target analytes can be anticipated by technicians at some point before analysis of an extracted sample is completed.

The IVME device can include a mono film of the absorbent gel or it can include a plurality of films overlaying the vial's inner surface, where the films are incapable of delamination from the vial's surface or an adjacent film. The plurality of films can be of like composition. The plurality of films can be of different composition, such that the affinity of one analyte is great for one film and lesser in another that has a strong affinity for a different analyte. The first deposited of a plurality of films may be a film that is deposited for bonding or binding to the vial's surface and is not necessarily contributing to the absorption of any analyte.

The absorbent gel can be deposited on the inner vial surface by dip coating, spray coating, spin coating, painting, or any other method to contact the vial with the sol. In a method, such as dip coating, the exterior of the vial can either be coated in addition to the inner surface, or the outer surface can be rendered incapable of having a gel formed on that surface by the sol. This can be carried out by modifying the external surface by an agent that reacts with otherwise reactive functionality on the surface or by coating the exterior with a coating that will not react with any components of the sol used to form the sorbent coating on the internal surface of the vial. Portions of the internal surface of the vial, such as, but not limited to, the base or the area near the entrance, can be modified in the manner described for the exterior portion if desired. For example, if it is advantageous that the sampling is only done by the lower portion of the vial but not the top portion only the lower portion can have a sol-gel coating formed thereupon. Alternatively, for example, where a stirring device is to be placed on the base during sampling or desorption of analytes and the sorbent coating would prohibit or otherwise inhibit stirring, the base could be rendered free of the sorbent coating by the manner in which the sol-gel coating is applied, for example where the vial is spun to force sol only to the surface parallel to the axis of rotation, or by spraying a sol on the non-base surface where that sol gels at a sufficient rate such that the non-sprayed base is effectively gel-free. Alternately, a solution that would degrade the sorbent coating could be place in only the bottom portion of the coated vial such that the sorbent coating from some base portion of the vial can be removed. For example, a dilute solution of hydrofluoric acid could be carefully placed on the base of a vial for a prescribed period that permits the selective degradation of the gel to the height of the solution placed in the vial. When deposition and cure of the gel and any desired modification is complete, the IVME device can be washed with one or more appropriate solvents, which can be a mixture or used sequentially, to remove unreacted precursors, deposition solvents, or side products, for example, cyclosiloxane or polymers capped with unreacted or incompletely reacted precursors. Additionally or alternatively, the prepared IVME device can be heated and/or evacuated to remove volatiles. Generally, but not necessarily, a solvent that is used for one or more washings is any solvent that is of the environment for testing, for example, water.

In an embodiment of the invention, the inner surface of the IVME device and the outer surface of the IVME device can be coated with different sorbent coatings. For example, one sol solution is placed in the vial to form an inner coated surface, and the capped vial can be dip-coated by a second sol solution to form an outer coated solution. In this manner the entire vial can be placed in a fluid environment to be sampled, and one or more analytes would be absorbed on the interior surface of the vial, and one or more other analytes would be absorbed on the exterior surface of the vial, permitting the desorption from the two surfaces to be carried out sequentially, as desired.

Figure 2:
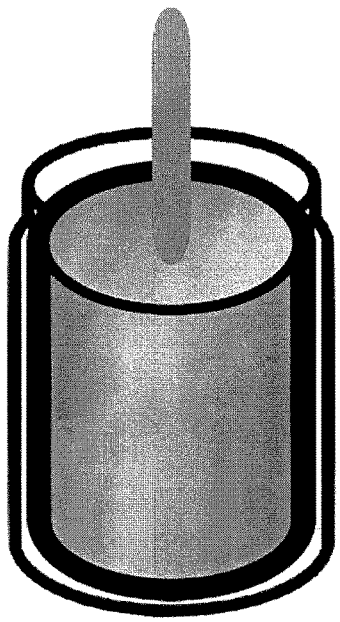
FIG. 2 shows a drawing of a spacer placed in an IVME device to reduce the liquid volume required for desorption, according to an embodiment of the invention.

During a solvent desorption of the analytes from the IVME device, a non-absorbent spacer, for example a Teflon cylinder or a polypropylene cylinder, can be placed within the IVME device, as illustrated in FIG. 2. The spacer can be particulate, and is used to decrease the volume available to the desorbing liquid In this manner, the desorbed sample solution can be more highly concentrated than one where the vial is used with no spacer to facilitate analysis of target analytes. The solvent can be placed in the IVME device such that it is only partially filled, and the IVME device can be rolled or shaken such that less than a full volume of liquid can desorb the analytes from the sorbent sol-gel coating. As with the spacer, the IVME device with an outer sol-gel coating that has absorbed a target analyte can be placed in a slightly larger vial with a solvent or solution to desorb the target analyte from the exterior sol-gel coating. The desorbing liquid can be a solvent or a solution, and it can contain an acid, a base, or a complexing agent to enhance desorption of a target analyte from the sorbent sol-gel coating.

The IVME devices can be constructed using EPA suggested glass containers for sampling. The sol-gel coating can include a generic coating for non-targeted analytes and a molecularly imprinted polymer for targeted analytes. After collecting an aqueous sample, a Teflon coated magnetic stirrer that is sterile can be inserted in the vial to hasten the achievement of extraction equilibrium. For targeted analysis using GC-MS or LC-MS, a singly or multiply deuterated standard of target analytes may be added to the sample to allow a rapid quantification by the ratio of molecular ion signals from the MS. After sampling by stirring for a prescribed period of time, the depleted sample matrix can be completely discarded by inverting the vial on a sterilized absorbent, such as, but not limited to a paper towel and the vail can be re-capped for storage before being back-extracted by solvent elution or by thermal desorption for analysis By practicing the sampling an analysis method employing IVME devices, the process from sample collection to usable analytical results becomes dramatically simplified. FIGS. 3A and 3B give comparable flow charts for state of the art SPE and using IVME sampling, according to an embodiment of the invention, respectively. The IVME method enables sampling and sample preparation in the field. The IVME method eliminates the necessity of filtration and post-sample preparation processes such as solvent evaporation and sample reconstitution. The IVME method eliminates expensive and labor-intensive processes such as addition of preservatives, transferring to the lab, storage at prescribed temperature, thawing, and extraction that is required by typical state of the art methods. The IVME method can eliminate errors involved in transportation, storage, and thawing. The IVME method significantly reduces the overall cost involved in the sample preparation process. The IVME method can facilitate forensic monitoring of illegal use of drugs and environmental monitoring.

Methods and Materials

Figure 4:
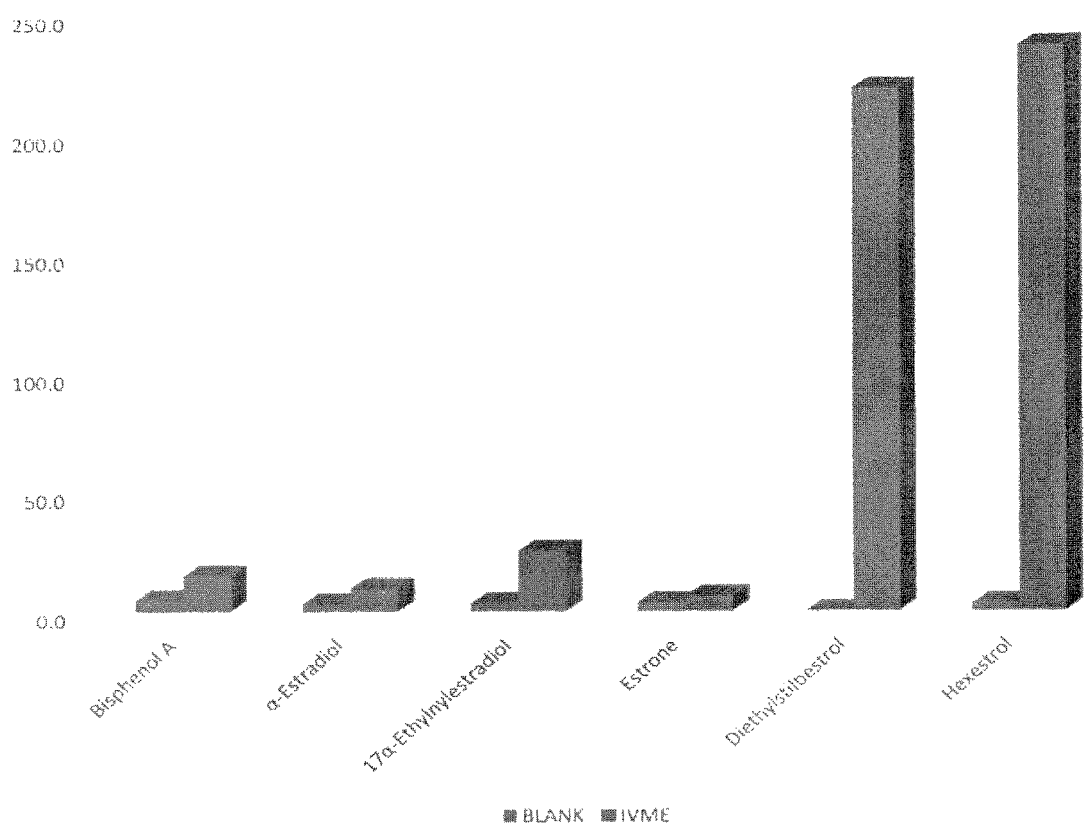
FIG. 4 shows analytical results for sampling collected in a vial and in an IVME device, according to an embodiment of the invention.

A mixture of bisphenol A, α-estradiol, 17α-ethylnylestradiol, estrone, diethylstilbestrol, and hexestrol in water was prepared with each component included at a concentration of 200 ng/mL. The mixture was sampled with an untreated (control) vial and an IVME device for sample collection. The IVME device was one where the sol-gel Poly(ethylene glycol) sorbent coating was prepared on the inner walls of a glass vial of equivalent dimensions and shape as the blank (40 mL, clear glass vial, O.D.×H 29 mm×82 mm, thread 24-400, PTFE/Silicone septum). FIG. 4 gives the results of the amounts extracted by the IVME device. The IVME was carried out by adding 30 mL of the sample solution containing 200 ng/mL of each of the test analytes for an hour. A Teflon-coated small bar magnet was used during the extraction process to diffuse the solution so that the sorbent coating inside the vial continuously receives fresh layer of the analyte solution to reach fast extraction equilibrium. Following the extraction, the aqueous solution of the analytes was discarded, extra water was vented by purging $N_2$ gas and a Teflon spacer was introduced into the vial to minimize the internal volume of the extraction vial. The extracted analytes were back-extracted into 1 mL of methanol, which was added gently into the vial containing the spacer. Finally, an aliquot of the methanol solution of the test analytes was injected into an HPLC-UV system for liquid chromatographic analysis. The same solution can be injected into a gas chromatographic system for gas phase separation and analysis. Alternately, the vial can be exposed to thermal shock for temperature-mediated desorption (thermal desorption) followed by gas chromatographic analysis.

It should be understood that the examples and embodiments described herein are for illustrative purposes only and that various modifications or changes in light thereof will be suggested to persons skilled in the art and are to be included within the spirit and purview of this application.

We claim:

1. An in-vial microextraction (IVME) device; comprising, a vial with at least a portion of the vial's inner surface bonded to a first sol-gel coating and at least a portion of the exterior surface bonded to a second sol-gel coating, wherein the first sol-gel coating is of different composition to that of the second sol-gel coating, wherein the first and second coatings comprise metal oxide comprising gels that absorb at least one target analyte.

2. The IVME device according to claim 1, wherein the vial is glass, plastic, ceramic, or metal.

3. The IVME device according to claim 1, wherein the metal oxide comprising gel is from at least one precursor of the structure: $R^1R^2R^3R^4M$, wherein: $R^4$ is optional; M is silicon, titanium, aluminum, zirconium, germanium, barium, gallium, indium, thallium, vanadium, cobalt, nickel, chromium, copper, iron, lanthanum, niobium, zinc, or boron; at least two of $R^1$, $R^2$, $R^3$, and $R^4$ are independently alkoxy, hydroxy, halides, hydrogen or dialkylamino, and remaining $R^1$, $R^2$, $R^3$, and $R^4$ are independently substituted or unsubstituted alkyl, aryl, cyanoalkyl, fluoroalkyl, phenyl, cyanophenyl, biphenyl, cyanobiphenyl, dicyanobiphenyl, cyclodextrin moieties, crown ether moieties, cryptand moieties, calixarene moieties, dendrimer moieties, graphene moieties, carbon nanotubes, or wherein the $R^1$, $R^2$, $R^3$, and $R^4$ is chiral or achiral and wherein at least one of the at least one precursor has at least three of $R^1$, $R^2$, $R^3$, and $R^4$ that are independently alkoxy, hydroxy, halides, hydrogen or dialkylamine.

4. The IVME device according to claim 3, wherein the metal oxide comprising gel further comprises a silicon oxide formed from a hydrolysis and condensation of a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tri(dialkyamino) alkylsilane, tri(dialkyamino)arylsilane, di(dialkyamino)dialkylsilane, di(dialkyamino)alkylarylsilane, di(dialkyamino) diarylsilane, or any combination thereof, wherein alkyl groups are $C_1$ to $C_4$ alkyl groups and aryl groups, phenyl groups, alkyl substituted phenyl groups, or polycyclic aromatic groups, wherein the alkyl groups and phenyl groups are unsubstituted or independently substituted with amino, hydroxyl, carboxylic acid, acid anhydride, epoxy, acrylate, methacrylate, vinyl, or reaction residue therefrom.

5. The IVME device according to claim 3, further comprising an organic portion, wherein the organic portion is oligomeric or polymeric.

6. The IVME device according to claim 5, wherein the organic portion comprises poly(ethylene oxide), polypropylene oxide, poly(ethylene oxide-co-propylene oxide), poly (butylene oxide), polyamide, polyester, or polybutadiene, where one or more carbons of the organic portion is unsubstituted or independently substituted with an amino, hydroxyl, carboxylic acid, acid anhydride, epoxy, acrylate, methacrylate, vinyl, or reaction residue therefrom.

7. The IVME device according to claim 3, wherein at least one of $R^1$, $R^2$, $R^3$, and $R^4$ independently comprises a bidentate ligand, polydentate ligand, crown ether, cryptand, aryene, graphene, fullerene, hydroxyfullerene, cyclodextrin, or calixarene.

8. The IVME device according to claim 1, wherein the inner surface in its entirety has the first sol-gel coating.

9. The IVME device according to claim 1, wherein the inner surface has the first sol-gel coating on the walls and no sol-gel coating on its base.

10. The IVME device according to claim 1, wherein the second sol-gel coating is of different composition to that of the first sol-gel coating.

11. A method of preparing an IVME device according to claim 1, comprising:
  providing a vial;
  depositing at least one sol solution on at least a portion of the inner surface and outer surface of the vial;
  curing the at least one sol into at least one first sol-gel coating on the inner surface of the vial and at least one second sol-gel coating on the outer surface of the vial; and
  optionally removing any unreacted portions of the sol or non-bound side products formed.

12. The method of preparing an IVME device of claim 11, wherein depositing comprises dip coating, spray coating, painting, filling the vial with the sol solution, or any combination thereof.

13. The method of preparing an IVME device of claim 11, wherein curing comprises an acid or a base catalyzed hydrolysis and condensation of oxide precursors; siloxy precursors; and/or organic precursors.

14. The method of preparing an IVME device of claim 13, further comprising an addition or polyaddition reaction catalyzed by an acid, a base, or a free radical initiator.

15. A method of sampling at least one target analyte, comprising:
  providing an IVME device of claim 1, wherein the first and second sol-gel coatings are absorbent of at least one target analyte;
  contacting the IVME device with a sample matrix suspected of containing the target analyte, wherein the sample matrix is a primary liquid, a primary suspension, or a secondary liquid or secondary suspension prepared by combining a primary solid with a provided liquid, wherein at least a portion of any of the at least one target analyte contained in the sample matrix suspected of containing the target analyte is absorbed in the FPSE sol-gel coating and
  optionally, separating the IVME device from the sample matrix suspected of containing the target analyte.

16. The method of sampling at least one target analyte of claim 15, wherein the sample matrix suspected of containing the target analyte comprises an aqueous solution or an aqueous suspension.

17. The method of sampling at least one target analyte of claim 15, wherein contacting comprises placing the sample matrix suspected of containing the target analyte in the IVME device.

18. The method of sampling at least one target analyte of claim 17, wherein placing the provided liquid in the IVME device is prior to placing the primary solid in the IVME device.

19. The method of sampling at least one target analyte of claim 15, wherein contacting further comprises stirring, shaking or agitating the IVME device containing the sample matrix suspected of containing the target analyte.

20. The method of sampling at least one target analyte of claim 15, wherein contacting comprises immersion of the IVME device in the primary liquid, the primary suspension, the secondary liquid, or the secondary suspension.

21. The method of sampling at least one target analyte of claim 15, further comprises adding a deuterated standard of a target analyte to the IVME device.

22. The method of sampling at least one target analyte of claim 15, wherein separating the IVME device from the sample matrix suspected of containing the target analyte comprises pouring or draining the primary liquid, the primary suspension, the secondary liquid, or the secondary suspension from the IVME device.

23. The method of sampling at least one target analyte of claim 22, wherein separating the IVME device from the sample matrix further comprises rinsing the IVME device with a tertiary liquid.

24. A method of analyzing for at least one target analyte, comprising:
  providing a sampling acquired according to claim 15;
  desorbing the target analyte from the IVME device; wherein desorbing comprises contacting one or more solvents and/or one a solution to the IVME device to form one or more analyte solutions or heating and/or evacuating the IVME device connected to a volatiles trap or an inlet of an analytical instrument; and
  introducing the analyte solution or contents of the volatile trap through an inlet of an analytical instrument.

25. The method of analyzing for at least one target analyte of claim 24, wherein the analytical instrument is a GC, LC, IMS, capillary electrophoresis unit, mass spectrometry (MS), GC-MS, or LC-MS.

26. An in-vial microextraction (IVME) device; comprising, a vial with at least a portion of the vial's inner surface bonded to a sol-gel coating and at least a portion of the exterior surface bonded to a second sol-gel coating, wherein the first sol-gel coating is of like composition to that of the second sol-gel coating, wherein the first and second sol-gel coatings comprise metal oxide comprising gels that absorbs at least one target analyte.

* * * * *